US009599576B1

(12) United States Patent
Portune et al.

(10) Patent No.: US 9,599,576 B1
(45) Date of Patent: Mar. 21, 2017

(54) ACOUSTIC—RF MULTI-SENSOR MATERIAL CHARACTERIZATION SYSTEM

(71) Applicants: Andrew Richard Portune, Oakdale, PA (US); Walter John Keller, III, Bridgeville, PA (US)

(72) Inventors: Andrew Richard Portune, Oakdale, PA (US); Walter John Keller, III, Bridgeville, PA (US)

(73) Assignee: Nokomis, Inc., Charleroi, PA (US)

( * ) Notice: Subject to any disclaimer, the term of this patent is extended or adjusted under 35 U.S.C. 154(b) by 212 days.

(21) Appl. No.: 14/199,072

(22) Filed: Mar. 6, 2014

Related U.S. Application Data

(60) Provisional application No. 61/851,324, filed on Mar. 6, 2013.

(51) Int. Cl.
*G01N 29/24* (2006.01)
*G01N 22/02* (2006.01)

(52) U.S. Cl.
CPC ............. *G01N 22/02* (2013.01); *G01N 29/24* (2013.01)

(58) Field of Classification Search
CPC ....... A01B 12/006; G01N 22/02; G01N 29/24
USPC .......................................................... 73/579
See application file for complete search history.

(56) References Cited

U.S. PATENT DOCUMENTS

| | | | |
|---|---|---|---|
| 5,170,666 A * | 12/1992 | Larsen | G01N 29/2418 73/571 |
| 5,218,294 A | 6/1993 | Soiferman | |
| 5,227,800 A | 7/1993 | Huguenin et al. | |
| 5,302,830 A | 4/1994 | Shivanandan | |
| 5,424,633 A | 6/1995 | Soiferman | |
| 5,517,110 A | 5/1996 | Soiferman | |
| 5,668,342 A | 9/1997 | Discher | |
| 5,714,888 A | 2/1998 | Naujoks | |
| 6,049,301 A | 4/2000 | Weagant | |
| 6,057,765 A | 5/2000 | Jones et al. | |
| 6,163,259 A | 12/2000 | Barsumian et al. | |
| 6,260,415 B1 * | 7/2001 | Goebel | G01D 5/48 73/582 |

(Continued)

FOREIGN PATENT DOCUMENTS

| JP | 06011530 | 1/1994 |
|---|---|---|
| JP | 200076387 | 3/2000 |

(Continued)

*Primary Examiner* — J M Saint Surin
(74) *Attorney, Agent, or Firm* — James Ray and Assocs; Alexander Pokot

(57) ABSTRACT

A system for determining properties and structural integrity of a material comprises a probe including a housing, a source operable to propagate an acoustic energy through a thickness of the material, a source operable to propagate a radio frequency (RF) energy through the thickness of the material, an acoustic member mounted within the housing and operable to measure a response of the material to the acoustic energy, and a radio frequency (RF) member mounted within the hollow interior in a close proximity to the acoustic member and operable to measure a response of the material to the RF energy. A hardware interface device is coupled to both acoustic and RF members. A controller is coupled to the hardware interface and configured to receive the acoustic and RF response signals and includes a processor operable to process the received acoustic and RF response signals.

17 Claims, 12 Drawing Sheets

(56) References Cited

U.S. PATENT DOCUMENTS

| | | |
|---|---|---|
| 6,496,703 B1 | 12/2002 | da Silva |
| 6,601,451 B1 * | 8/2003 | Roberts ................ G01N 29/041 |
| | | 73/579 |
| 6,720,905 B2 | 4/2004 | Levitan et al. |
| 6,759,863 B2 | 7/2004 | Moore |
| 6,765,527 B2 | 7/2004 | Jablonski et al. |
| 6,823,736 B1 * | 11/2004 | Brock ................ G01N 29/0609 |
| | | 73/587 |
| 6,825,456 B2 | 11/2004 | Chadwick et al. |
| 6,897,777 B2 | 5/2005 | Holmes et al. |
| 6,927,579 B2 | 8/2005 | Blades |
| 6,985,771 B2 | 1/2006 | Fischell et al. |
| 7,130,624 B1 | 10/2006 | Jackson et al. |
| 7,138,936 B2 | 11/2006 | Duff et al. |
| 7,188,037 B2 | 3/2007 | Hidehira |
| 7,391,356 B2 | 6/2008 | Brumley et al. |
| 7,512,511 B1 | 3/2009 | Schultz et al. |
| 7,515,094 B2 | 4/2009 | Keller, III |
| 7,609,199 B2 | 10/2009 | Nishijima et al. |
| 7,639,178 B1 | 12/2009 | Mulbrook et al. |
| 7,654,148 B2 * | 2/2010 | Tomlinson, Jr. ....... G01N 29/07 |
| | | 73/801 |
| 7,777,671 B2 | 8/2010 | Schnitzer et al. |
| 7,777,672 B2 | 8/2010 | Schnitzer et al. |
| 7,844,341 B2 | 11/2010 | Von Arx et al. |
| 8,063,813 B1 | 11/2011 | Keller |
| 2005/0265124 A1 | 12/2005 | Smith |
| 2006/0152232 A1 | 7/2006 | Shevets et al. |
| 2007/0027643 A1 | 2/2007 | Lesesky et al. |
| 2007/0279071 A1 | 12/2007 | Orton |
| 2008/0103555 A1 | 5/2008 | Dicks et al. |
| 2009/0049920 A1 * | 2/2009 | Young ................ G01N 29/07 |
| | | 73/649 |
| 2010/0123453 A1 | 5/2010 | Pauly et al. |
| 2010/0125438 A1 | 5/2010 | Audet |
| 2011/0095757 A1 * | 4/2011 | Nielsen ............ G01R 33/5617 |
| | | 324/303 |
| 2011/0320170 A1 | 12/2011 | Pathak et al. |
| 2012/0223403 A1 | 9/2012 | Keller, III |
| 2012/0226463 A1 | 9/2012 | Keller, III |
| 2012/0245860 A1 * | 9/2012 | Keely ................ F01D 21/003 |
| | | 702/35 |
| 2012/0291553 A1 * | 11/2012 | Balasubramaniam G01N 29/069 |
| | | 73/625 |

FOREIGN PATENT DOCUMENTS

| | | |
|---|---|---|
| JP | 2003503679 | 1/2003 |
| JP | 2011174709 | 9/2011 |
| JP | 2012026913 | 2/2012 |
| KR | 100946238 | 3/2010 |
| KR | 101077441 | 10/2011 |

* cited by examiner

ACOUSTIC—RF MULTI-SENSOR MATERIAL CHARACTERIZATION SYSTEM

CROSS-REFERENCE TO RELATED APPLICATIONS

This application is related to and claims priority from U.S. Provisional Patent Application Ser. No. 61/851,324 filed on Mar. 6, 2013.

FIELD OF THE INVENTION

The present invention relates, in general, to non destructive evaluation of materials and, more particularly, this invention relates to a system for a non-destructive evaluation of materials that employs acoustic and radio frequency (RF) sensors and yet, more particularly, the instant invention provides a system, employing acoustic and RF sensors, that measures critical material properties while locating and identifying defects that degrade performance of the material.

STATEMENT REGARDING FEDERALLY SPONSORED RESEARCH AND DEVELOPMENT

N/A

REFERENCE TO SEQUENCE LISTING, A TABLE, OR A COMPUTER PROGRAM LISTING COMPACT DISC APPENDIX

N/A

BACKGROUND OF THE INVENTION

As is generally well known, the performance of materials employed in military and civilian application relies upon their structural integrity and a range of mechanical, thermal, and electrical material properties. Nondestructive evaluation (NDE) is critical to the success of systems or applications which these materials are integrated in as it allows them to be tested after deployment, storage, repairs, manufacturing, and prior to, during, and after their use in application. As such, there is a clear need for an NDE characterization system capable of determining material properties while simultaneously locating and identifying defects which limit material performance. However, to the best knowledge of the Applicant, individual established NDE techniques are incapable of providing both defect detection while simultaneously delivering mechanical, thermal, and electrical properties, as many are specialized towards a particular end or property subset. Technologies used to assess critical material properties often cannot locate and identify structural flaws while methods used to locate flaws cannot measure material properties needed to determine performance and expected lifetime. Therefore, there is a need for a multi-sensor approach combining acoustic and radio frequency (RF) NDE techniques to directly address this problem and provide a complete assessment of the material, including all properties relevant to performance prediction, while attaining superior sensitivity to minute material defects.

Ultra-sensitive sensor systems and their supporting algorithms are currently used in a range of nondestructive characterization settings where acoustic and/or electromagnetic emissions are detected and analyzed to perform material or system assessments. State-of-the-art systems can employ embedded FPGA-based signal assessment algorithms for real-time analysis of RF or acoustic data streams. Results from existing systems have demonstrated extremely high correlation of detection outputs with reality in controlled studies, with false alarm rates consistently near 0% and probability of detection close to 100% for well characterized subjects. Mature algorithmic processes have demonstrated a readily adaptable capability for advanced analysis of received signal data in real time. Ultra-sensitive sensor technology has achieved success both in field applications and the manufacturing environment. Existing sensor systems have been ruggedized to maintain accuracy and integrity of system components in the field.

Advanced materials used in critical commercial and military technologies require structural integrity to provide exceptional performance in a demanding environment. Determination of material properties must be conducted using NDE techniques to enable tested materials to be directly implemented into their intended systems. Currently available systems fall short of the needs of modern materials as they cannot simultaneously measure the entire range of relevant material properties while locating and identifying structural defects that degrade performance. Therefore, an acquisition of this information is needed to meet the growing needs of quality control standards and ensure that systems will achieve mission goals and/or product requirements.

SUMMARY OF THE INVENTION

The invention provides a multi-sensor nondestructive characterization system that synergistically combines information from acoustic and RF test techniques to perform high fidelity assessment of both multilayer and monolithic materials. Results from each technique provide feedback that is exploited to deliver highly reliable material property measurements, identify defects below the resolution limit of single-technique methodologies, and perform quality assessment. The dual-modality of the multi-sensor system provides increased sensitivity to microstructural parameters, including, but not limited to secondary phase inclusions, porosity, voids, fiber-matrix disbonds, stacking sequence in multi-layer laminates, fiber type and volume fraction, matrix properties, internal fractures, surface cracks, dislocation density, trans-laminar cracks, moisture ingress, and impact damage, providing a substantial improvement over current state-of-the-art NDE systems. Combining information from both sensor modalities enables highly accurate measurements of materials properties including, but not limited to compositional makeup, phase concentration, elastic moduli, strength, fracture toughness, hardness, thermal diffusivity, thermal conductivity, complex permittivity, and complex permeability. Other thermal, mechanical, and electrical material properties are also accessible either directly or indirectly through data fusion of acoustic and RF characterization results. Materials properties are extractable for individual layers in multilayer stack-ups through computational application of algorithmic analyses.

Existing ultra-sensitive embedded system hardware, architecture, and analysis algorithms are employed as the foundation of the disclosed invention. Specific system components, architecture, and algorithms are selected for the combination and analysis of acoustic and RF data streams. Software enables rapid material assessments and result display for real-time feedback on material condition. Novel structural elements of the disclosed invention include dual element probe head design for simultaneous characterization with multiple NDE modalities and data fusion of acoustic and RF test results for higher probability of defect detection with lower false alarm rate.

The system addresses the current needs of quality assurance for materials used in systems which cannot be allowed to fail.

OBJECTS OF THE INVENTION

It is, therefore, one of the objects of the present invention to provide a system for a non destructive evaluation (NDE) of materials that employs acoustic and radio frequency (RF), defined as the frequency range from 10 KHz to 300 GHZ, sensors and/or techniques.

Another object of the present invention is to provide an acoustic-RF multi-sensor sensor system for NDE of materials that uses common embedded hardware components to drive both acoustic and RF sensors and to reduce computational requirements, system weight, and cost.

Yet another object of the present invention is to provide an acoustic-RF multi-sensor system for NDE of materials that is capable of characterizing a broad range of materials, including metals, ceramics, composites, polymers, and hybrids.

Another object of the present invention is to provide an acoustic-RF multi-sensor sensor system for NDE of materials that is installed on a multi-axis gantry apparatus for linear movement across the width, length, or height of the material supported by the gantry.

A further object of the present invention is to provide an acoustic-RF multi-sensor system for NDE of materials, that determines critical material properties while locating and identifying structural defects that degrade performance of the material(s) under test.

Yet a further object of the present invention is to provide an acoustic-RF multi-sensor system for NDE of materials, that employs a defect response library to classify detected defects and that can be populated through multiple means, including but not limited to, experimental testing, theoretical calculations, and data from other systems and/or methods.

Another object of the present invention is to provide an acoustic-RF multi-sensor sensor system for NDE of materials that detects defect types including, but not limited to pores, voids, solid inclusions, cracks, fiber-matrix disbonds, delaminations between material layers, and surface imperfections.

Another object of the present invention is to provide a method for NDE of materials with acoustic-RF multi-sensors, that executes data fusion algorithms including, but not limited to Bayesian statistics, Bayesian networks, Artificial Neural Networks (ANN), and Gaussian Mixture Models.

Yet another object of the present invention is to provide a method for NDE of materials with acoustic-RF multi-sensors, that analyses acoustic attenuation coefficient spectra for determination of defect characteristics such as composition, geometry, and orientation within the bulk material.

A further object of the present invention is to provide a method for NDE of materials with acoustic-RF multi-sensors, that performs acoustic testing analysis including, but not limited to, time of flight testing, acoustic velocity analysis, acoustic spectroscopy, acoustic backscatter analysis, peak amplitude testing, and background noise analysis.

Yet a further object of the present invention is to provide a method for NDE of materials with acoustic-RF multi-sensors, that performs RF and electrical properties analysis including, but not limited to, microstrip testing, transmission line techniques, parallel plate capacitor testing, scattering parameter analysis, and dielectric spectroscopy.

Another object of the present invention is to provide an acoustic-RF multi-sensor that utilizes common processing assets to include, but not limited to Digital Signal Processing (DSP), Field Programmable Gate Array (FPGA), microprocessor and/or microcontrollers for the processing of both the RF and acoustic data collected by the multi-sensor.

A further object of the present invention is to provide an acoustic-RF multi-sensor that parallelizes the acoustic and RF chains in a common processing architecture and fuses the results in at the end of the parallel chains to achieve improved data throughput and overall multi-sensor performance.

In addition to the several objects and advantages of the present invention which have been described with some degree of specificity above, various other objects and advantages of the invention will become more readily apparent to those persons who are skilled in the relevant art, particularly, when such description is taken in conjunction with the attached drawing Figures and with the appended claims.

BRIEF DESCRIPTION OF THE VARIOUS EMBODIMENTS OF THE INVENTION

Figure 1A:
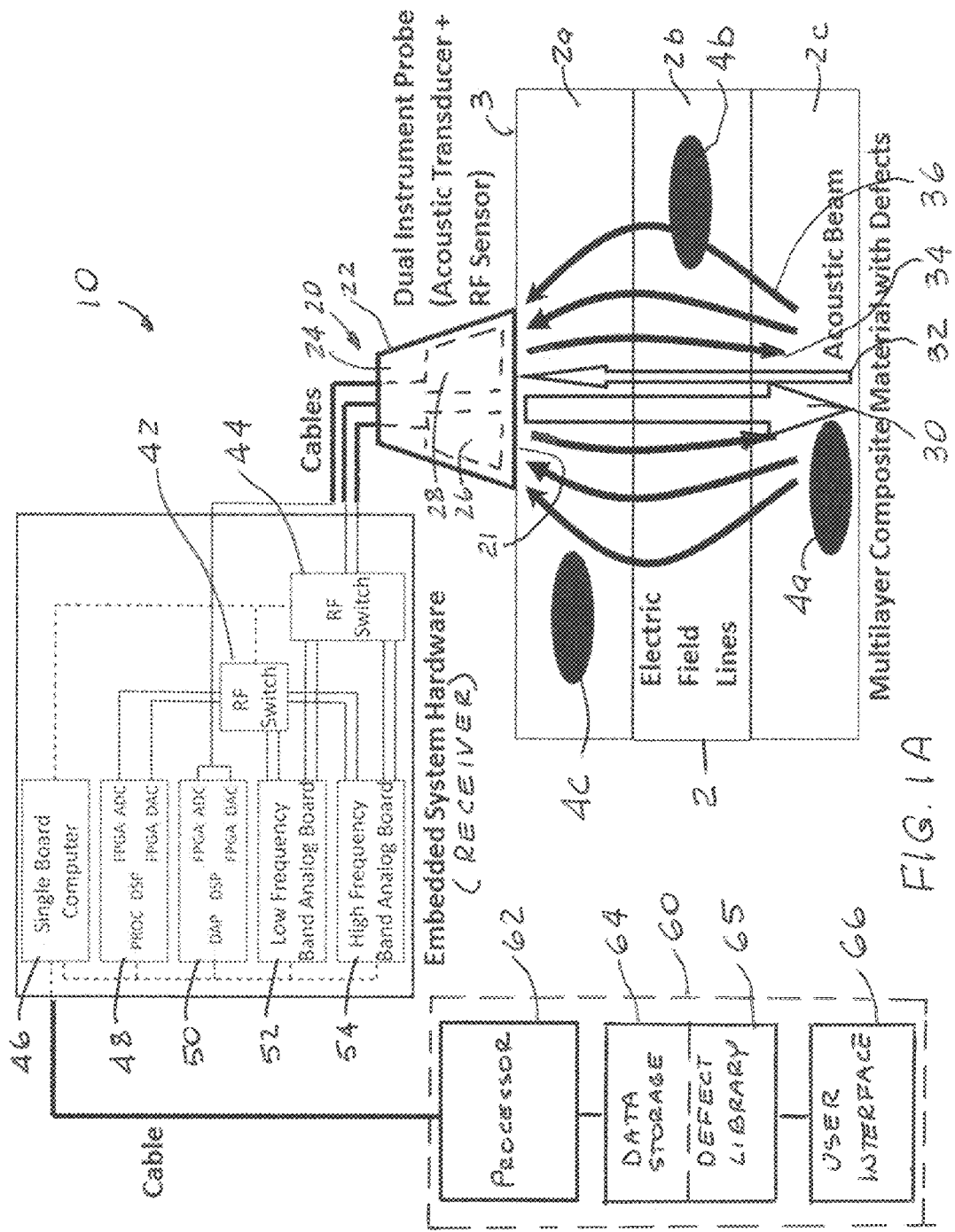
FIG. 1a is a diagram of an acoustic-RF multi-sensor nondestructive characterization system constructed in accordance with one form of the invention.

Prior to proceeding to the more detailed description of the present invention, it should be noted that, for the sake of clarity and understanding, identical components which have identical functions have been identified with identical reference numerals throughout the several views illustrated in the drawing figures.

The present invention is illustrated and described in combination with a multi-layer material 2, although it will be apparent to those skilled in the relevant art that the present invention may be applied to other materials and, as such, should not be interpreted as a limiting factor of the present invention.

Reference is now made, to FIGS. 1-10, wherein there is shown a multi-sensor system, generally designated as 10, hereinafter referred to as a "system", for determining properties and structural integrity of the material 2, shown by way of one example in FIG. 1a as comprising multiple layers 2a, 2b and 2c. More specifically, the system 10 is configured to detect, measure, characterize and maps defects 4a and 4b that may be disposed within a thickness of the material 2, as shown in FIG. 1a, or on a surface or surfaces thereof and is further configured to determine properties of the material 2 in either a homogeneous or layer manner.

The multi-sensor system 10 includes a dual-instrument probe, generally designated as 20, hereinafter referred to as a "probe". The probe 20 includes a housing 22 having a hollow interior 24. An acoustic member 26 and a radiofrequency (RF) member 28 are mounted within the hollow interior 24 in a tandem arrangement with and in a close proximity to each other. The acoustic member 26 may be either of the type that is operable to only transmit acoustic energy, only receive the acoustic energy or both. By way of one example only, the acoustic member 26 may be a transducer. The RF member 28 may be either of a type that is operable to only transmit RF energy, only receive the RF energy or both. By way of another example only, may be as a microstrip, an antenna or a waveguide.

The described invention requires both acoustic and RF non-destructive evaluation (NDE) characterization results, and as such both acoustic and RF members, 26 and 28 respectively, are required to be present in the probe 20 in a complimentary type arrangement to each other. The particular configuration of the probe 20 may be specified to meet the particular needs of an application with the only restriction being access to the material under test by both acoustic and RF members, 26 and 28 respectively.

In one form of FIG. 1a, the probe 20 is shown as having a surface 21 thereof being positioned in a contact with a surface 3 of the material 2. Although the probe 20 has been shown as being positioned above the thickness of the material 2 it can be also positioned below such thickness. Furthermore, the probe 20, used to characterize the material 2, could be configured in other multiple ways in relation to the material 2 under test, including, but not limited to: air-coupled, liquid-coupled, pulse-echo, through-transmission, pitch-catch, and in arrays of one or more instruments.

During a test, acoustic energy 30 and RF energy 34 are introduced into the material 2, wherein each energy interacts with the material 4 and wherein the acoustic energy feedback 32 and RF energy feedback 36 are received by the probe 20. The probe 20 is contemplated to utilize commercially available and/or customized acoustic and RF members, 26 and 28 respectively.

The system 10 also includes a receiver, generally designated as 40, that is connected via cable or cables to the probe 20. The receiver 40 comprises embedded hardware interface including, but is not limited to, a single board computer, RF switches, analog boards covering different frequency ranges, analog to digital converters (ADC), field programmable gate arrays (FPGA), and digital signal processors (DSP). In an exemplary embodiment of FIG. 1a, the receiver 40 includes RF switches 42 and 44 and a plurality of boards 46, 48, 50, 52, and 54 that are operatively coupled to one or both RF switches 42 and 44. Thus, common embedded hardware components are used to drive both testing techniques provided by acoustic member so as to reduce computational requirements, system weight, and cost. By running both characterization techniques using the same embedded hardware interface 40, the system 10 is lightweight, man-portable, and non-hazardous to operating personnel, requiring no special equipment to use safely.

The system 10 also includes a controller 60 that is coupled to the receiver 40 and that is configured to analyze acoustic and RF signals received by the probe 20 and is further configured to control operation of the acoustic member 26 and the RF member 28. The controller 60 may be, without limitations, a computer, laptop, or tablet. It would be understood that the controller 60 includes at least a processor 62, a data storage 64 and a user interface 66. The instant invention also contemplates that the controller 60 can be integrated with the receiver 40 into a single control apparatus.

The system 10 is preferably a modular system, making it flexible to address a range of different problems and/or issues. Specific characteristics of acoustic and RF members, 26 and 28 respectively, are varied for applicability to different material conditions including, but not limited to composition, thickness, density, number of layers, porosity, and damage state.

In a further reference to FIG. 1a, the operation of the one or both acoustic member 26 and the RF member 28, can be varied, for example as by frequency settings, to attain a specific penetration of the acoustic energy 30 or RF energy 34 into the material 4, wherein such energy feedbacks 32 and 36 are either from a specific layer, for example layer 2c of FIG. 1a, and wherein such energy feedbacks are solely from the surface 3 of the material 2.

Figure 1B:
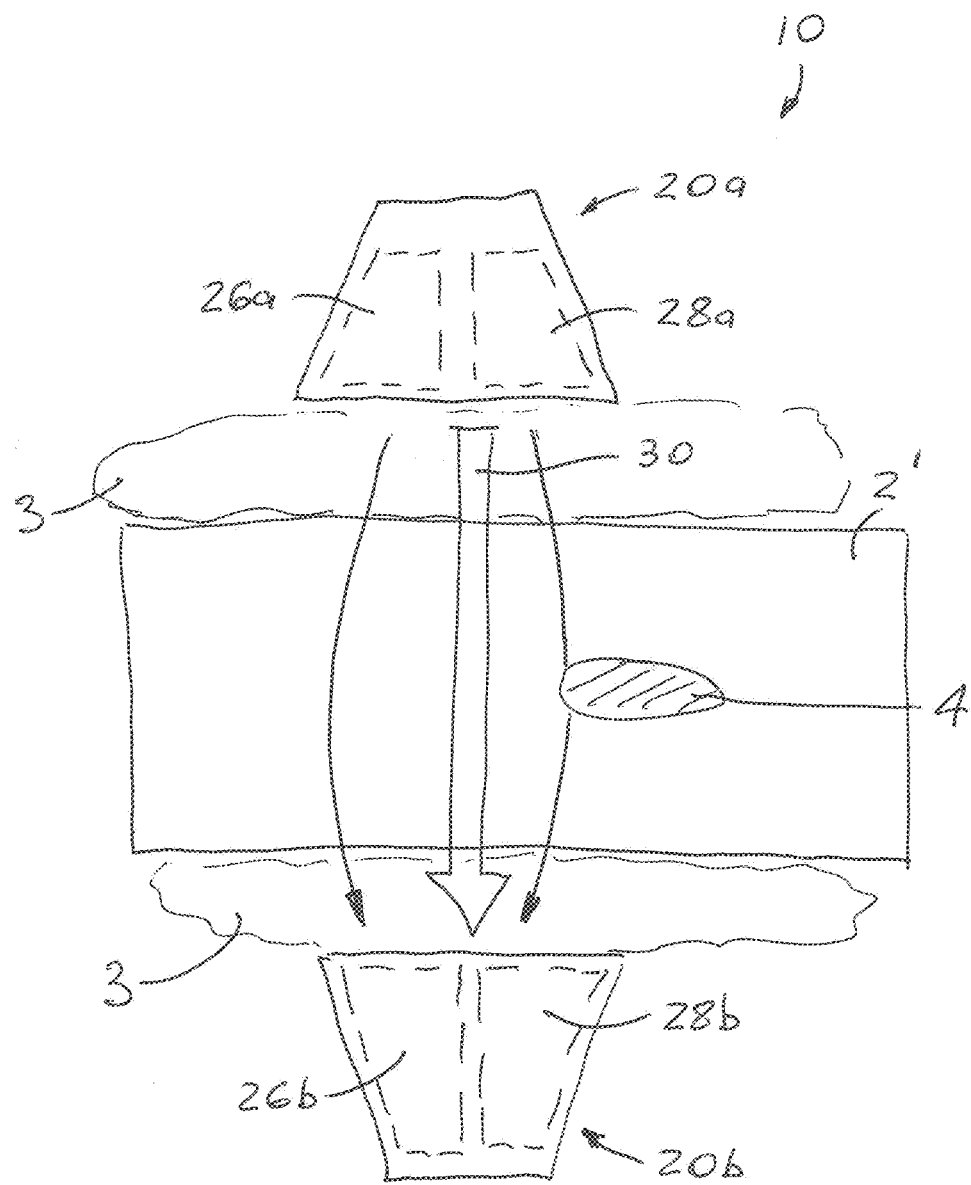
FIG. 1b is a diagram of an acoustic-RF multi-sensor nondestructive characterization system constructed in accordance with another form of the invention.

FIG. 1b illustrates another form of the invention using a probe 20a as a transmitter of both acoustic and RF energies by including acoustic transmitter 26a and RF transmitter 28a and using the probe 20b as a receiver of both acoustic and RF energies by including the acoustic receiver 26b and RF receiver 28b. Probes 20a, 20b are further illustrated as spaced from the respective surface of the material 2', shown as a single layer material with the defect 4. In this form, the acoustic energy 30 and RF energy 34 propagate through the thickness of the material 2'.

Figure 2:
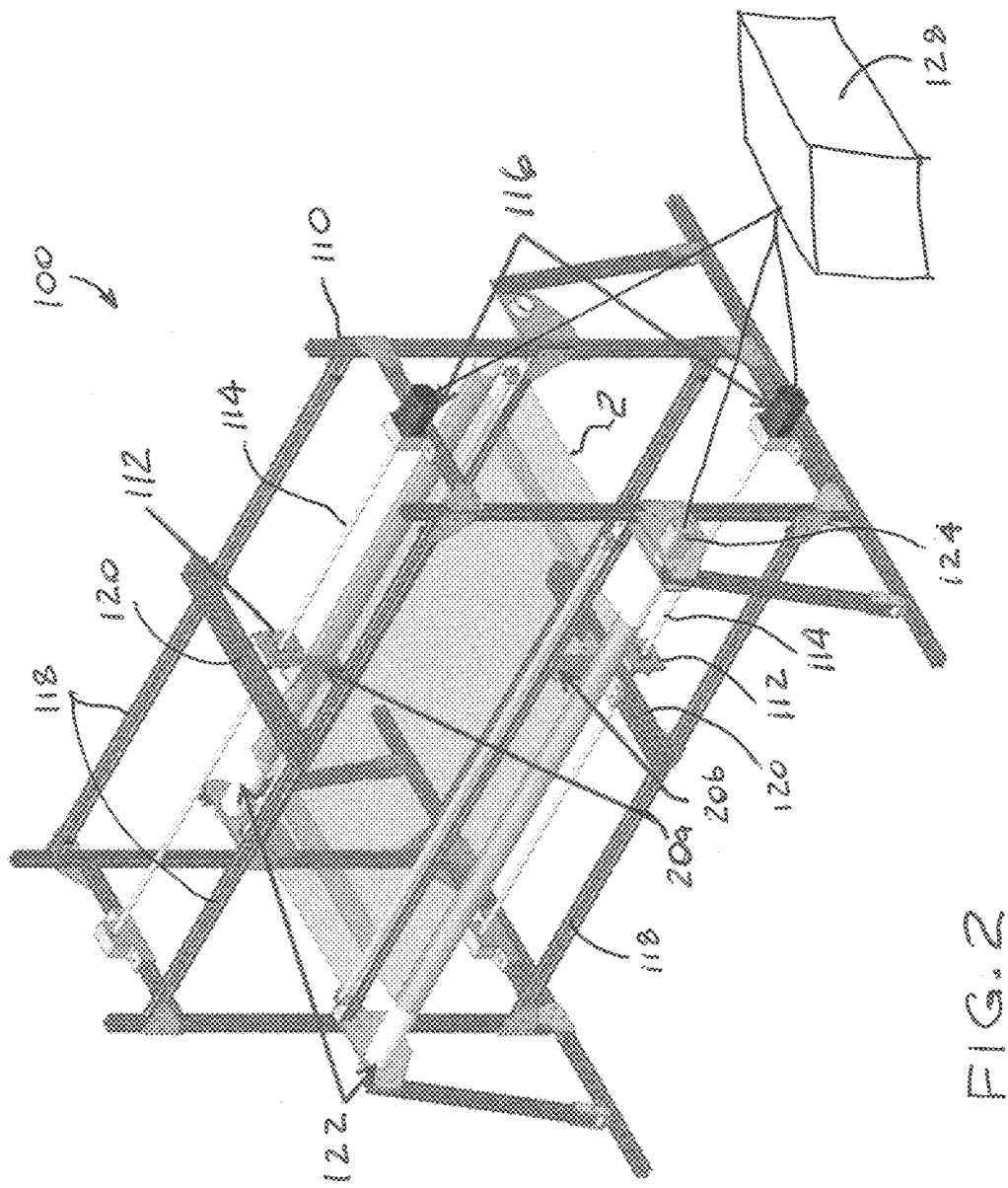
FIG. 2 shows a dual-instrument probe of FIG. 1b installed on a single axis scanning gantry in a through-transmission test configuration.

Now in a particular reference to FIG. 2, the system 10 is illustrated as being integrated with a multi-axis linear motion gantry, generally designated as 100, so as to provide maps of measurement results at varying spatial and frequency resolutions by making multiple detailed measurements over a defined area. As an example, FIG. 2 shows a diagram of dual instrument probes 20a and 20b connected to the gantry frame 110, of at least a single-axis linear motion type, in a through-transmission test configuration. More particularly, each probe 20a or 20b is mechanically attached to a block 112 that translates on a linear component 114, for example such as a drive screw, that is rotated by a motor 116. It would be understood that block 112, the linear component 114 and the motor 116 define a linear drive actuator that can be represented by any known linear drive actuator. The block 112 is also mechanically coupled to the guides 118 by way of a member 120. The material 2 under test is shown as being disposed on the spools 122, one of which is rotated by the motor 124. Also, the spools 122 have been shown in FIG. 2 as physically integrated into the gantry 100, such spools 122, or any other means for either moving or supporting material, may be provided as a separate assembly. For example, the gantry 100 may be positioned in a relationship with a manufacturing line (not shown) so as to accommodate material 2 manufactured in a roll form on such manufacturing line. Preferably, the instant invention requires that the probes 20a and 20b are mounted for the reciprocal linear movement across the width of the material 2 under test.

In the embodiment of FIGS. 1a and 2, the probe 20a is provided as a transmitter of both acoustic and RF energies and the probe 20b is provided as a receiver of both acoustic and RF energies. Both probes 20a and 20b will be then coupled to the controller 60. However, both probes 20a, 20b can be configured to transmit and receive acoustic and RF energies, so as to increase the speed of testing the material 2 or to increase the confidence of defect finding and material property characterization.

The probes 20a, 20b and the components of the gantry 100 of a mobile type of FIG. 2 can be powered using a portable power source 128, including, but not limited to, a generator, battery, or vehicle alternator to enable field testing in remote locations. The system 10 of a stationary type can be powered by conventional standard power outlets.

It is also contemplated that the material 2, 2' may be tested during a manufacturing process. In this application, the gantry 100, or a similar arrangement, will be adapted to accommodate continuous feed of such material 2, 2'.

The system 10 is capable of characterizing a broad range of materials 2, including, but not limited to metals, ceramics, composites, polymers, and hybrids. The system 10 is particularly advantageous in testing composite or multi-layer type material 2 of FIG. 1a. For example, such multi-layer material 2 may be provided as RF shielding material having a fiber layer 2b sandwiched between resin layers 2a and 2c.

As has been described above, settings of the acoustic and RF members, 26 and 28 respectively, are selected to maximize sensitivity to structural defects, microstructural parameters, and material properties for the material under examination. More specifically, settings of the acoustic and RF members, 26 and 28 respectively, include, but are not limited to acoustic transducer frequency range, acoustic transducer focal distance, acoustic transducer faceplate area, RF member frequency range, RF member bandwidth, RF member area, the applied data fusion algorithm, algorithmic weighting parameters, and algorithm operation parameters. Selection of particular settings follows empirical study of the material system in question. Parametric testing is performed on a standard sample set to identify a parameter space which provides the highest resolution microstructural parameter extraction, material property definition (mechanical, thermal, and electrical), and defect sensitivity.

During material analysis and testing, one or more probe 20 are positioned for efficient coupling of acoustic and RF energy into the material 2, 2' under investigation. The number of required members 26, 28 is determined by the specific material 2, 2' under test and a specific test configuration. The advantage of using more than one probe 20 during the test is a shorter test time required to fully characterize the material volume of interest as multiple locations could be characterized simultaneously, in a parallel type processing mode.

Each probe 20 may be positioned in a direct physical contact with the material 2, 2', as shown in FIG. 1a or a coupling medium 3 such as air, water, polymer blocks, or other materials may be used between the probe 20 and material 2, 2', as shown in FIG. 1b. Once coupling is complete, acoustic and RF characterization techniques are performed to extract relevant information from the material 2, 2' of interest. Acoustic testing techniques include, but are not limited to, time of flight testing, acoustic velocity analysis, acoustic spectroscopy, acoustic backscatter analysis, peak amplitude testing, and background noise analysis. RF and electrical properties methodologies include, but are not limited to, microstrip testing, transmission line techniques, parallel plate capacitor testing, scattering parameter analysis, and dielectric spectroscopy. Analysis techniques are performed for test results, including, but not limited to, determination of elastic parameters from acoustic velocity data, measurement of material layer thicknesses from time-of-flight data, determination of dielectric permittivity from scattering parameters ($S_{11}$, $S_{21}$), determination of particle size distributions from acoustic spectroscopy curve fitting, and classification of anomalous behavior based on characteristic signal responses which include, but are not limited to peak strength, peak structure, harmonic relationships, frequency distribution, power spectral density, and acoustic velocity (surface, shear and longitudinal). Results from analyses are used to specify parameters for the material 2, 2' under test which can be used for multiple applications, including, but not limited to, mechanical property prediction, thermal property prediction, electrical property prediction, Remaining Useful Life (RUL) prediction, and defect detection and classification.

Figure 3A:
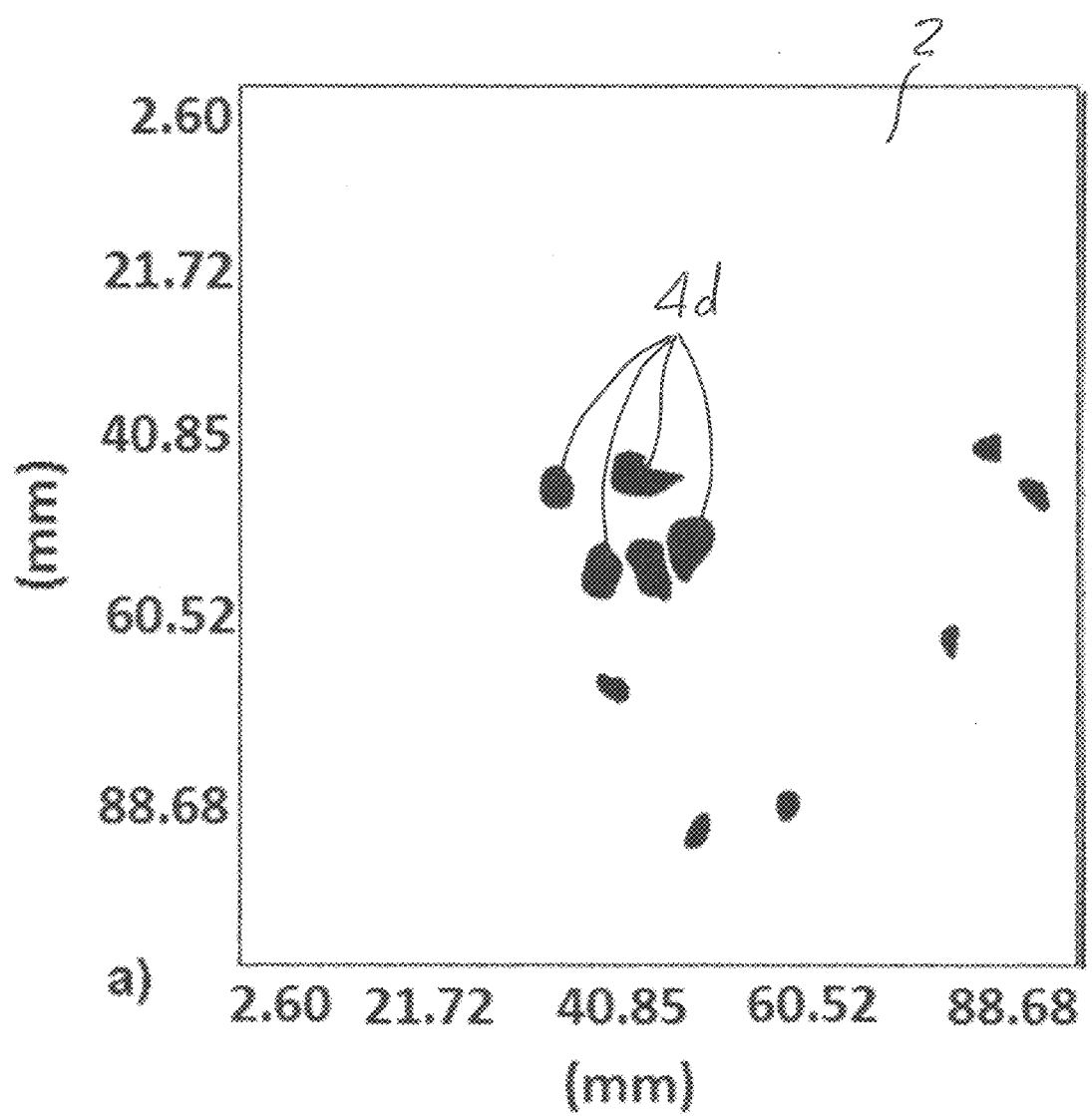
FIG. 3a illustrates defects detectable in a monolithic material and their respective energy loss signatures.
Figure 3B:
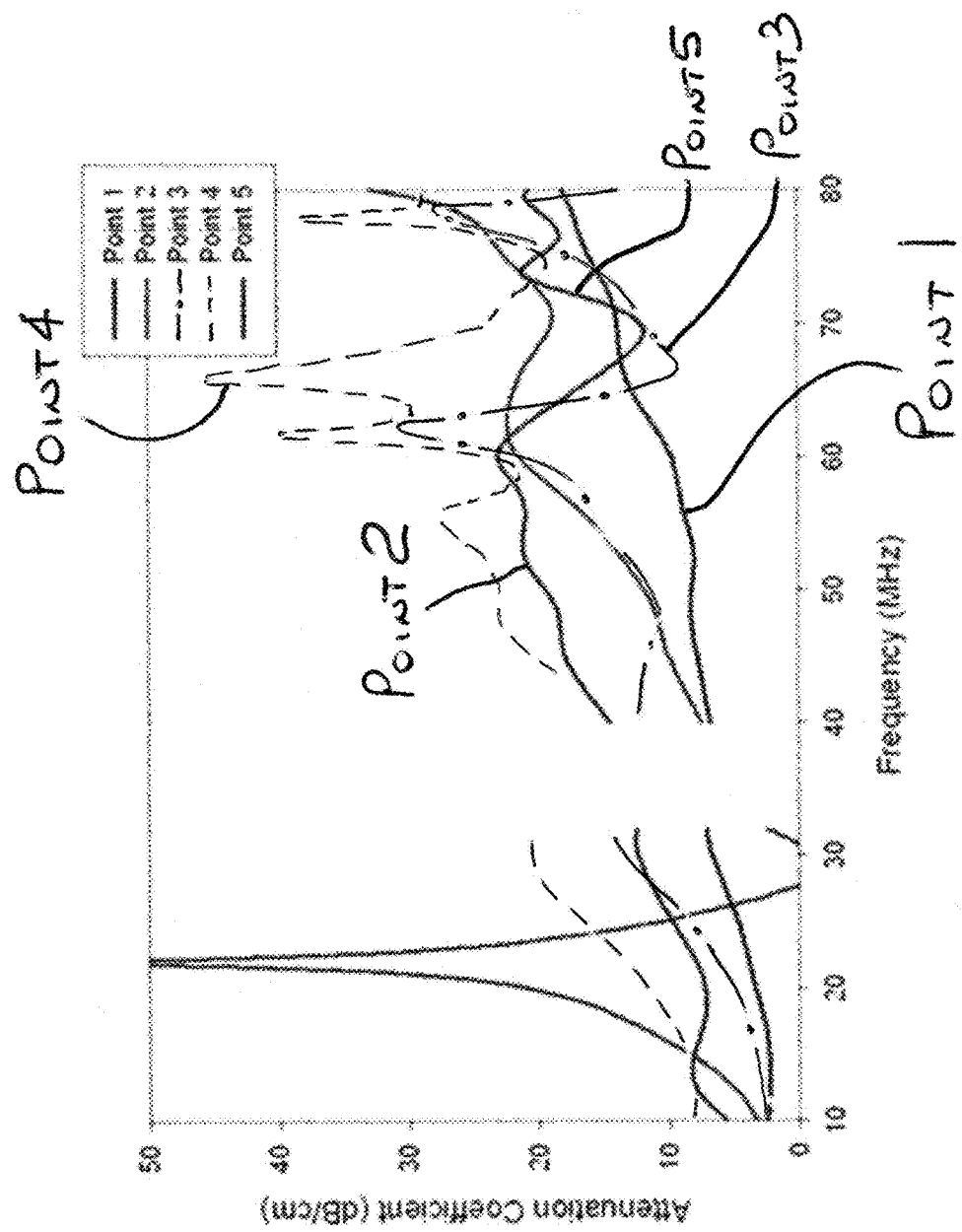
FIG. 3b illustrates acoustic signatures measured using acoustic spectroscopy associated with each defect.

Preliminary results on locating and identifying defects through techniques incorporated into the system 10 are defined by acoustic attenuation coefficient C-scan map in FIGS. 3a-3b. As illustrated in FIG. 3b, five defects (points 1-5) were located using scanning methodology as indicated by a substantial increase in an overall signal attenuation coefficient. The map shown in FIG. 3a illustrates the identification of a material property gradient while also detecting multiple structural defects 4d. Determination of the material homogeneity state enables performance prediction and improves quality control of sub-optimal product. Each line graph shown in FIG. 3b corresponds to one of the defects 4d detected in the material 2. Each line acts as a signature which is causally dependent on defect geometry and composition. Analysis of defect signatures is enhanced through combination of RF spectral measurement data in the same material volume as the inclusion of additional information provides higher confidence in statistical classification and improves sensitivity to minute defect sizes.

Figure 4:
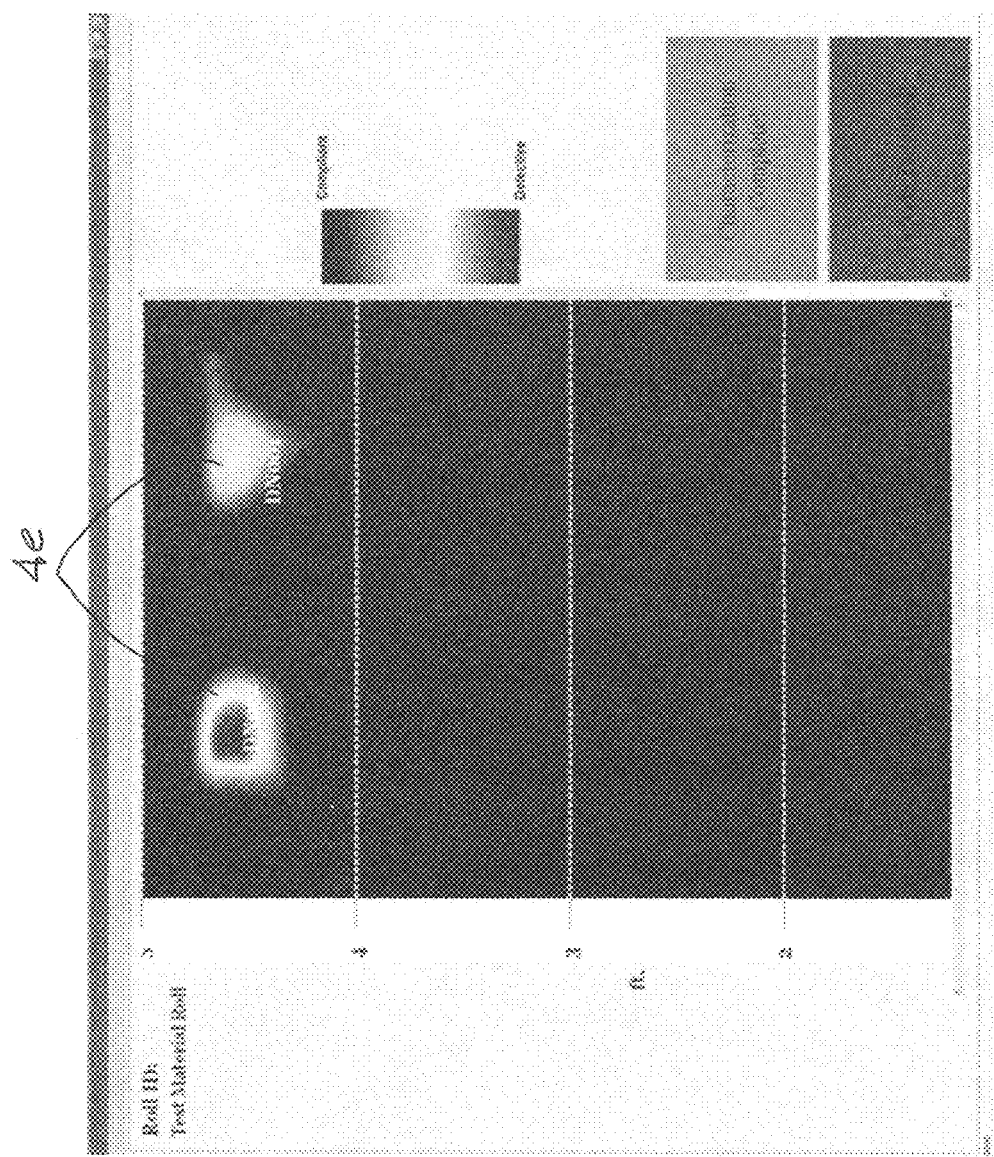
FIG. 4 shows defects detected in EMI shielding material by RF through-transmission measurements.

Acoustic spectroscopy identified acoustic signatures which are characteristic of each defect type. Analysis techniques for assessment of acoustic spectra through techniques incorporated into the system 10 can be performed for determination of defect characteristics such as composition, geometry, and orientation within the bulk material. Spectra are incorporated into a defect response library to enable rapid identification of similar flaws detected in future materials characterization experiments. Defects 4e detected in composite Electromagnetic Interference (EMI) shielding material using RF through-transmission techniques are shown in FIG. 4. Similar to FIG. 3, specific characteristics of the defects 4e detected in the RF scan can be determined via analysis of the RF and acoustic energy loss signatures through techniques incorporated into the system 10, with data fusion enhancing defect sensitivity and facilitating flaw classification.

The invention provides a defect response library 65 to classify detected defects. Such defect response library 65 can be populated through multiple means, including, but not limited to experimental testing, theoretical calculations, and references from other work. The defect response library 65 can be populated with a mix of acoustic test defect responses, RF test defect responses, and dual acoustic-RF test defect responses. It would be understood that such defect response library 65 resides within the controller 60 and, more particularly, in association with the data storage 64.

Applicants found that acoustic energy loss spectra measured through acoustic spectroscopy, which is not a common techniques for NDE testing of solid material, are causally dependent on the entirety of the bulk microstructures. Internal flaws below traditional resolution limits will still cause a characteristic loss of acoustic energy as ultrasonic waves propagate through the material. Deconvolution of acoustic energy loss spectra enables these flaws to be located and identified.

Figure 5A:
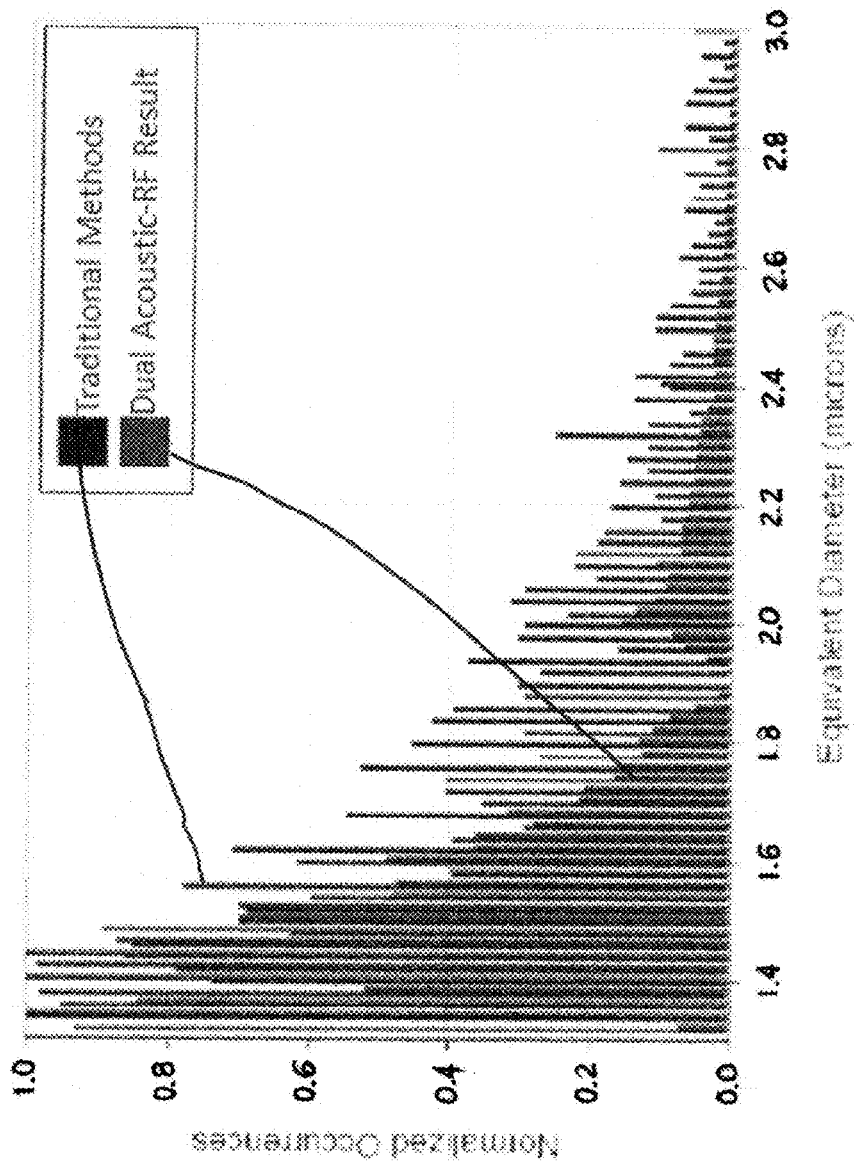
FIG. 5a illustrates exemplary results for a microstructural parameter extraction.
Figure 5B:
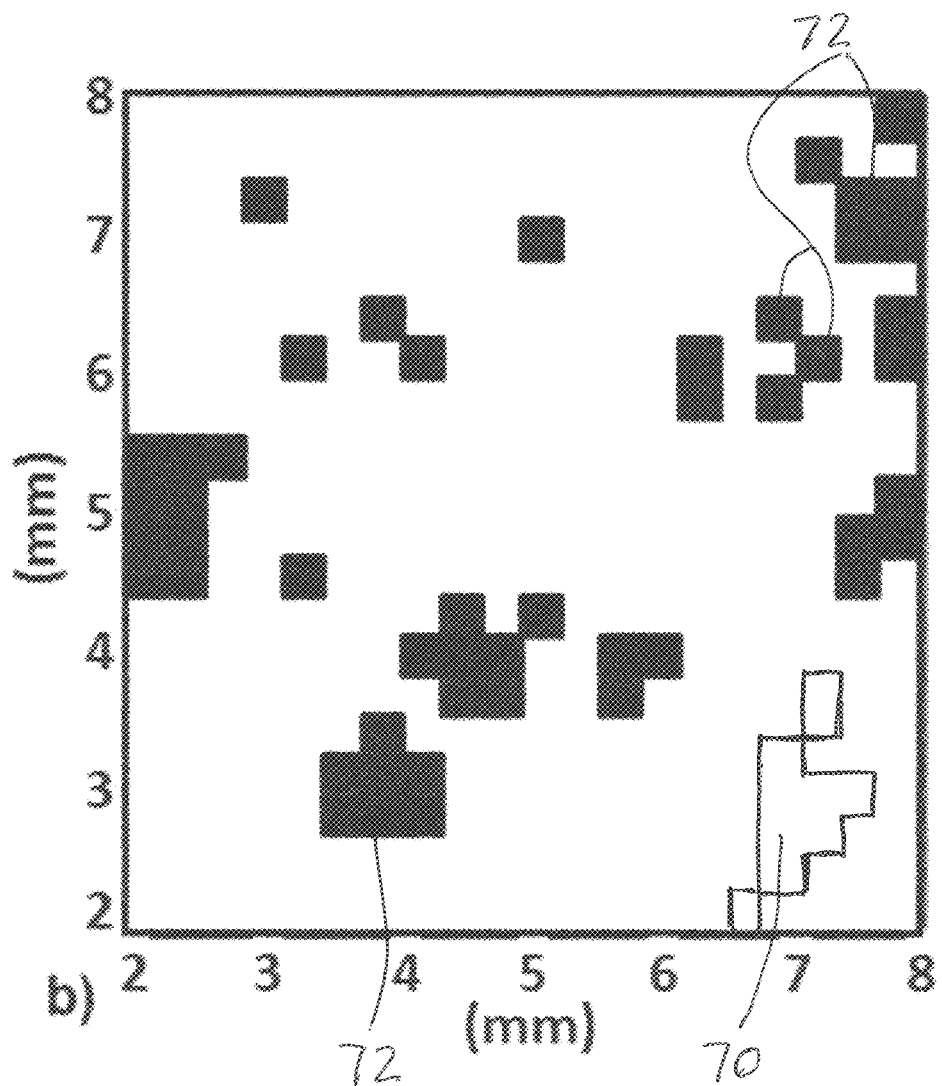
FIG. 5b illustrates an exemplary map of mean grain size variations.

Flaw identification through spectroscopic analysis forms a core capability of the invented system 10, and can be applied to a range of different defect types and matrix materials. Detectable defect types include, but are not limited to, pores, voids, solid inclusions, cracks, fiber-matrix disbonds, delaminations between material layers, and surface imperfections. FIG. 5a illustrates results from acoustic characterization showing how size distribution content can be obtained from this methodology. By making measurements over a large sample area, the invented multi-member system can create multi-dimensional maps of critical microstructural parameters such as the mean inclusion size, mean grain size, and/or porosity, such as the one shown in FIG. 5b. The resulting color map in FIG. 5b corresponds to the gradient in microstructural parameter measured by the invention, with red areas 70 indicating, for example, a high concentration of performance limiting inclusions and blue areas 72 indicating areas of a low concentration. Maps of thermal, electrical, or mechanical materials properties can be made using the acoustic-RF fusion results provided by the invention. Property maps can be directly input into finite element models to increase their capabilities and performance prediction accuracy.

Figure 6:
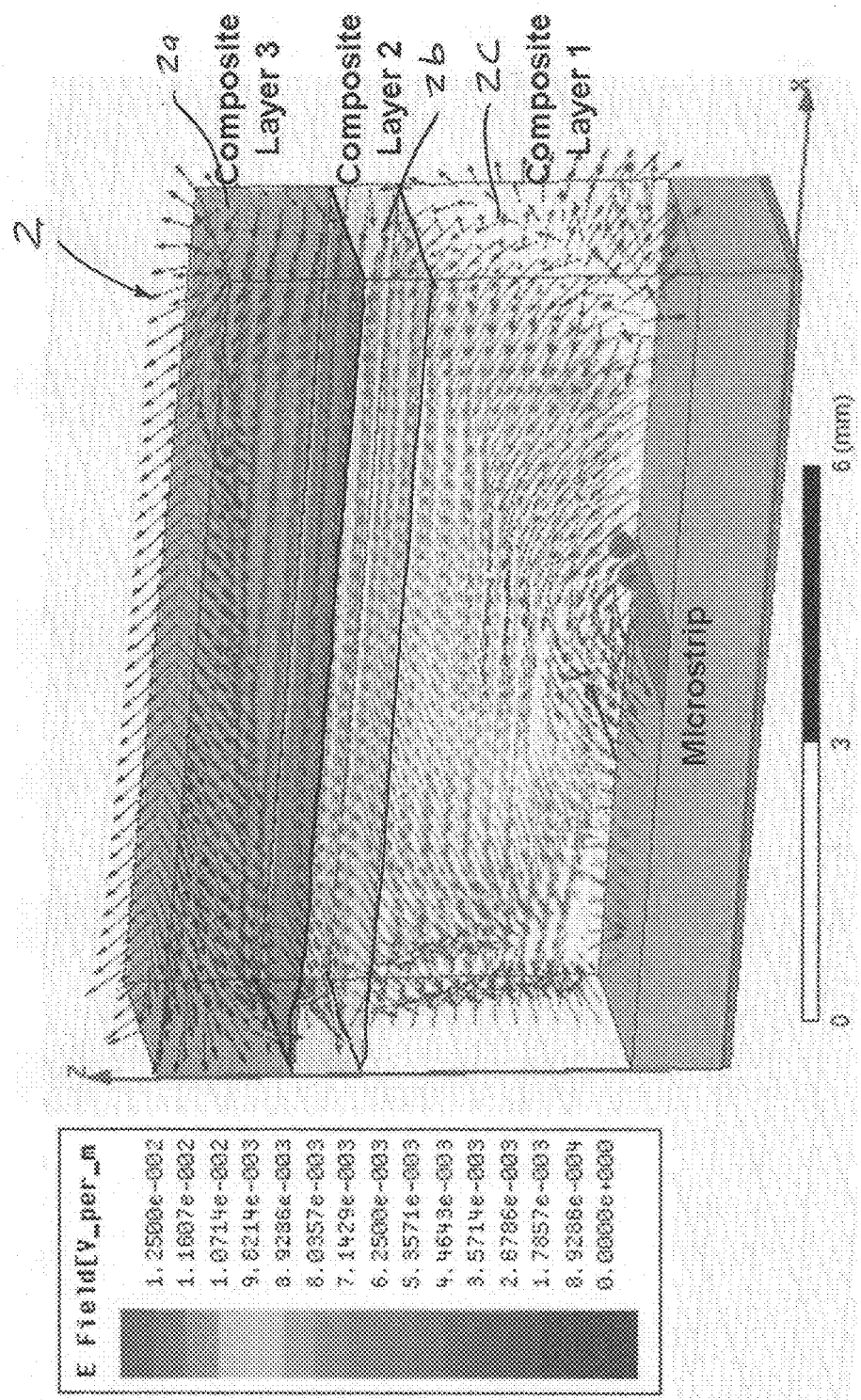
FIG. 6 is a model of electric field vectors propagating through a multilayer composite material system.

It has been found that the system 10 increases the accuracy and sensitivity of established acoustic techniques through inclusion of RF characterization data. RF characterization techniques such as microstrip through transmission line testing create electromagnetic fields which interact with surface and bulk (thickness) features of the material 2 under test and/or examination. Measured scattering parameters are dependent on the material thickness, number of material layers, layer compositions, and the presence and location of flaws (discontinuities). Modeling results showing the variation of electric field vectors in a defect-free three layer composite material stack-up are shown in FIG. 6. The inclusion of any defects 4 within the structure of the material 2, 2' would alter the direction and intensity of the electromagnetic field interactions in a manner characteristic to the specific defect, enabling their classification and parameter extraction.

It has been found that the system 10 achieves a greater property measurement accuracy and sensitivity to minute flaws through a data fusion of information received from acoustic and RF members, 26 and 28 respectively, used of both transmittal and receipt of the respective energy in FIGS. 1a, 1b. Results from each member are combined and are used complimentarily in analysis; the synergy and feedback of dual-modality testing is exploited to provide a high definition and thorough characterization of the material 2, 2' of interest. This is accomplished through a data fusion algorithm that efficiently combines acoustic and RF characterization results to provide a coherent and plausible assessment of the material. Data fusion algorithms incorporated into the system 10 may include, but are not limited to Bayesian statistics, Bayesian networks, Artificial Neural Networks (ANN), and Gaussian Mixture Models.

Figure 7:
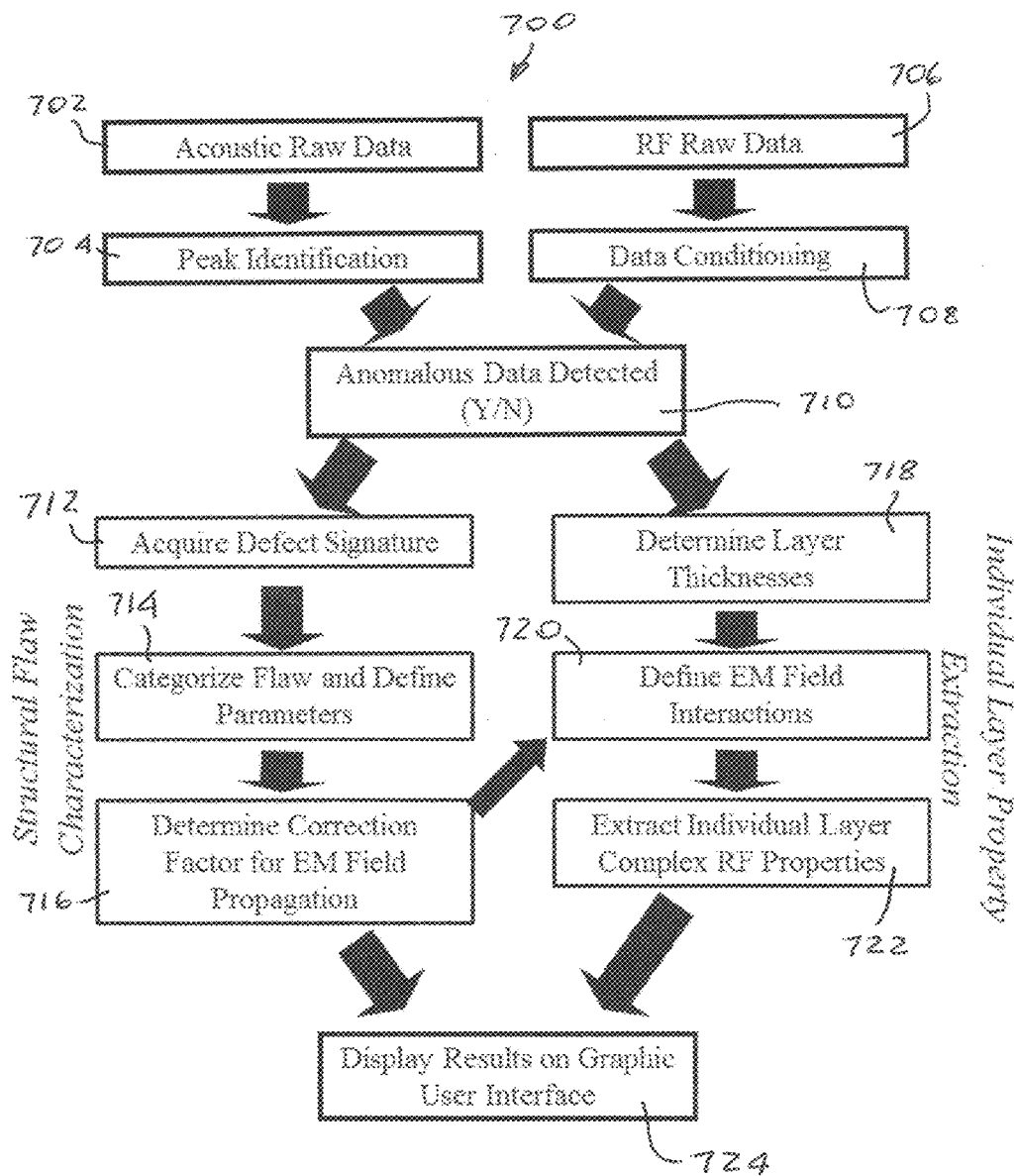
FIG. 7 is a flowchart a the data fusion algorithm employed by the system of FIG. 1.

A flowchart with the basic outline of the data fusion algorithm, generally designated as 700, is shown in FIG. 7. The dual pathways indicate the logic which the algorithm follows depending on whether anomalous data is measured, where anomalous is defined as unexpected data given properties and parameters of the material 2, 2'. The data fusion algorithm initially considers raw data acquired from acoustic member 26 in step 702 and RF member 28 in step 706. The processor 62 determines the peaks of the acoustic raw data in step 702 and converts RF signal from time domain to frequency domain in step 708. Then, in step 710, an anomalous data is sought based upon a priori information regarding the material 2, 2' in question, such as its compositional family, and an understanding of expected test results. Statistical analysis of initial raw data determines the probability of internal and surface defects based upon the presence of anomalous defects in all examined characterization modalities. The left path, including steps 712, 714, and 716, illustrates the logic which is followed if anomalous data is measured. The defect is identified and classified in terms of characteristic parameters which include, but are not limited to, composition, size, and geometry. This information is then included in determination of electromagnetic field interactions with the material layers to determine material properties which include, but are not limited to, mechanical, thermal, and electrical properties. In step 716, determination of defect parameters is necessary prior to material property determination as the defect physically alters the EM field interaction, resulting in different test results than if the defect were not present.

If defects are not detected, analysis proceeds towards extraction of relevant material properties. Material layer thicknesses are determined, in step 718, through acoustic time of flight methodology, while compositional information and relative phase concentration is procured through analysis of measured acoustic velocities and acoustic spectroscopy results. Frequency dependent acoustic energy attenuation provides additional information on primary and secondary phase characteristics. Acoustic spectroscopy delivers microstructural parameters including, but not limited to, average grain size, grain size distribution, porosity, secondary inclusion phase, average secondary inclusion size, and secondary inclusion size distribution. In step 720, acoustic results are employed to explicitly determine the electromagnetic (EM) field interaction volume in each material layer. Explicit definition of this volume facilitates inclusion of RF characterization techniques by identifying relative contributions to measurement results from each material layer in step 722. Analysis of RF scattering parameters across multiple frequency epochs provides additional information necessary to determine mechanical, electrical, and thermal material properties with high fidelity. Results from dielectric spectroscopy provide additional verification of relevant microstructural parameters for increased accuracy. Results can be displayed on the user interface 66 in step 724.

Figure 9:
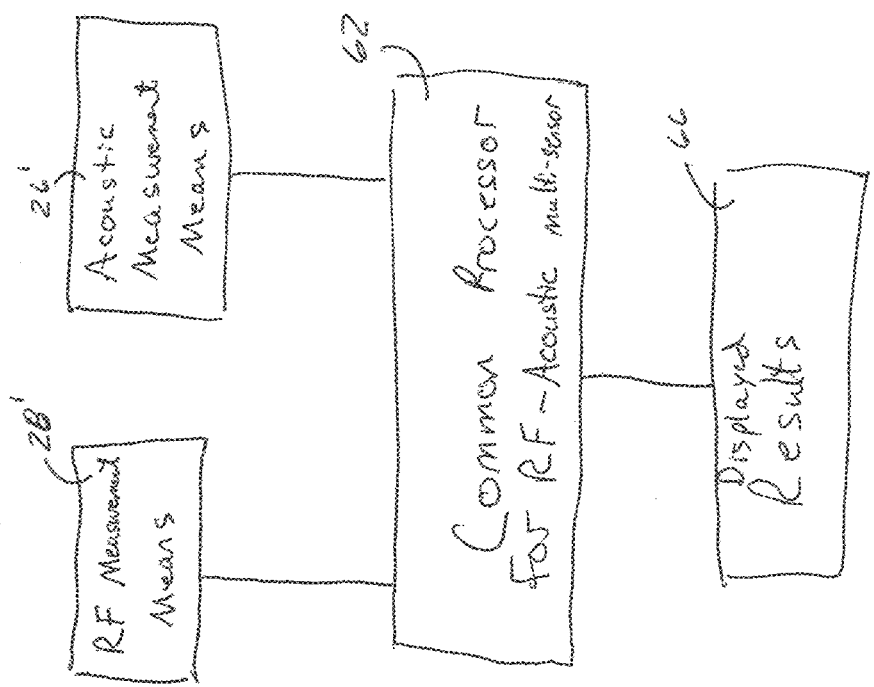
FIG. 9 illustrates a block diagram of another form of the invention.

Thus, in one form of FIG. 9, the acoustic member 26, receiver 40 provide acoustic measurement means 26' and the RF member 28 and receiver 40 provide RF measurement means 28'. The data from the acoustic measurement means and RF measurement means are processed by a common processing means 62, wherein the common processing means 62 processes both the RF and the acoustic data for determining the properties and the structural integrity of the material 2 in a non-destructive material evaluation manner. The results can be displayed on the display 66.

Figure 10:
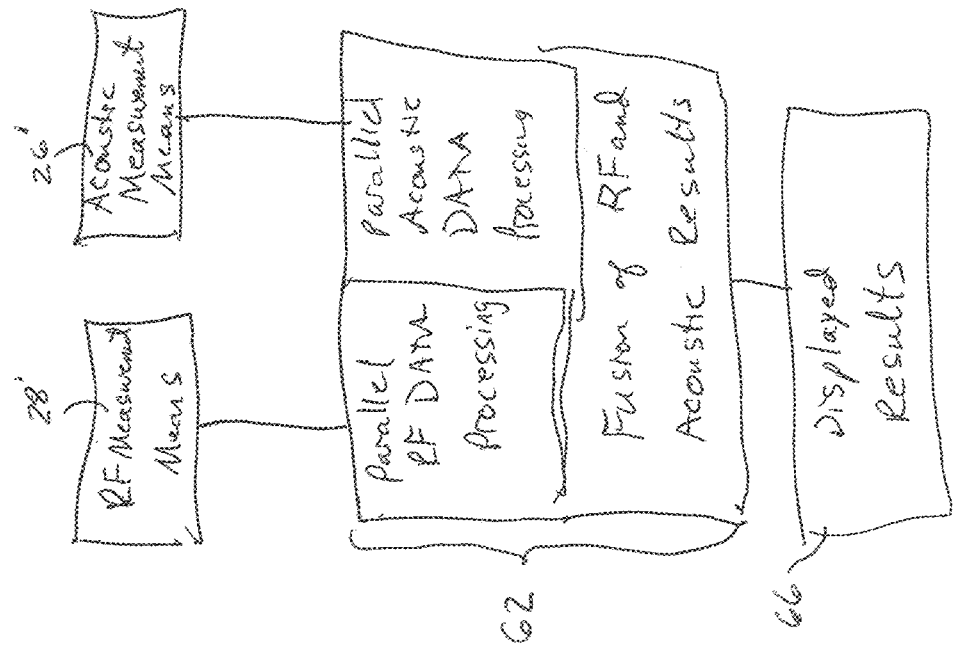
FIG. 10 illustrates a block diagram of another yet form of the invention.

In another form of FIG. 10, the acoustic member 26, receiver 40 provide acoustic measurement means 26' and the RF member 28 and receiver 40 provide RF measurement means 28'. The common processing means 62 is configured to process data from the RF measurement means 28 and the acoustic measurement means 26 in parallel with one another and fuse the processed data later in a processing chain to achieve improved performance of the system 10. The results can be displayed on the display 66.

Figure 8:
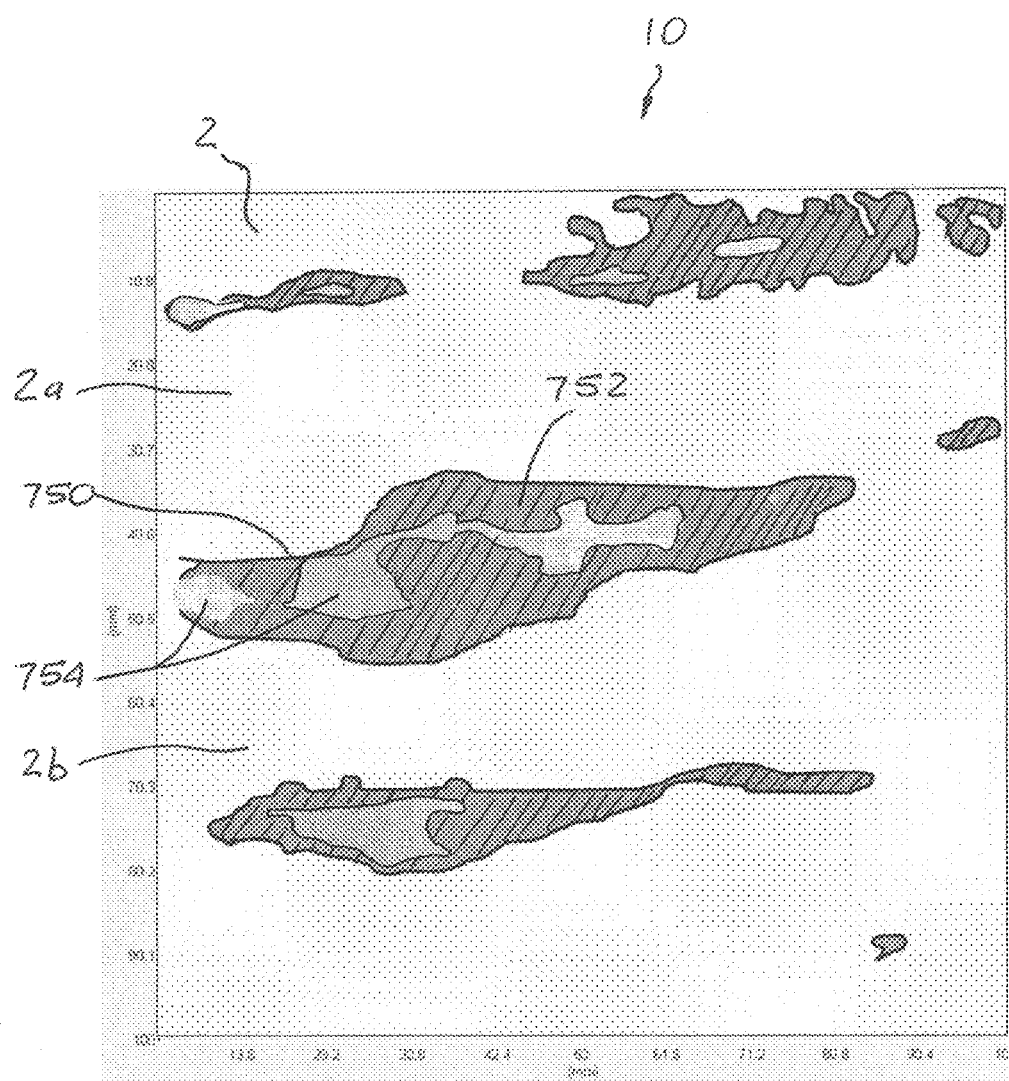
FIG. 8 is an exemplary map of delaminations detected in a multilayer material.

FIG. 8 illustrates one example of defect structure characterized by the system 10 in accordance with the above referenced algorithm, wherein the outline 750 defines a boundary between two layers, 2a and 2b. The reference numeral 752 defines a region with insufficient quantity of adhesive boding the layers 2a and 2b together, while reference numeral 754 defines a region with the amount of adhesive exceeding the designed requirement.

If the probability of surface or bulk defects is high, as determined through analysis of raw acoustic and RF characterization results, data analysis logic first focuses on specification of flaw parameters before proceeding to extraction of material properties. Defect signatures acquired through application of acoustic spectroscopy are used in conjunction with RF frequency domain response to define flaw parameters including, but not limited to composition, geometry, orientation, and depth from the sample surface. This information enables determination of the acoustic and electromagnetic field interaction volumes for the material under examination, where the interaction volume is defined as the precise volume of the material through which the acoustic or electromagnetic energy passes.

When defects are present, knowledge of flaw characteristics are necessary for determination of interaction volumes as electromagnetic and acoustic waves are diffracted or distorted through interactions with anomalous irregularities in the material. Once interaction volumes are defined, correction factors are calculated and applied to determine mechanical, electrical, and thermal material properties of interest with high fidelity.

Results from modeling and simulation may be used in specific materials 2 of interest to streamline identification of EM and acoustic interaction volumes, increasing the efficiency and rapidity of characterization analyses. Modeling and simulation, while helpful, is not required for accurate characterization of materials using the instant system 10.

Existing ultra-sensitive embedded system hardware, architecture, and analysis algorithms are employed as the foundation of the disclosed invention. Specific system components, architecture, and algorithms have been optimized for the combination and analysis of acoustic and RF data streams. Software enabling rapid material assessments and result display has also been based on existing software employed in previously mentioned existing ultra-sensitive member systems.

In one embodiment, the disclosed invention provides a multi-member nondestructive characterization platform that combines advanced acoustic and radio frequency (RF) characterization techniques to deliver a unique hybrid nondestructive test capability. The combination of multiple NDE methodologies enhances defect detection by providing sensitivity to flaws beneath the detection resolution of individual techniques via data fusion algorithms. In addition, combination of NDE methodologies provides a complete material property determination which cannot be achieved through individual techniques due to their limited scope. The system 10 applies acoustic spectroscopy to identify bulk material phases, determine particle size distributions, and identify characteristic defect signatures. As an orthogonal measurement, RF testing results are used to verify and expand upon information discovered in acoustic tests by providing greater sensitivity to different kinds of structural flaws. The combination of acoustic and RF testing enables high fidelity measurements of mechanical, thermal, and electrical properties. Additionally, the employed dual-modality ensures that the system 10 is sensitive to both surface and bulk (thickness) features, minimizing the probability that a performance limiting flaw is not detected. The system 10 exhibits a considerable increase in sensitivity for defect detection, accuracy of flaw classification, and confidence in test results, as shown in Table I. Preliminary results in identifying defect signatures and mapping delaminations in multilayer materials systems are shown in FIGS. 3 and 8.

TABLE I

| | Comparison of NDE capabilities | | | | | | | |
|---|---|---|---|---|---|---|---|---|
| | Layer Thickness | Porosity | Composition | Flaw Size Distribution | Phase Identification | Defect Classification | RF Properties | Most Complete Analysis |
| Traditional Ultrasonic Methods | ☒ | ☒ | ☒ | ☐ | ☐ | ☐ | ☐ | ☐ |
| Acoustic Spectroscopy | ☒ | ☒ | ☒ | ☒ | ☒ | ☒ | ☐ | ☐ |
| RF Characterization | ☐ | ☐ | ☐ | ☐ | ☒ | ☒ | ☒ | ☐ |
| Nokomis' Multi-Sensor System | ☒ | ☒ | ☒ | ☒ | ☒ | ☒ | ☒ | ☒ |

The system 10 leverages existing state-of-the-art embedded system hardware components to drive each characterization technique, vastly reducing system costs and weight. Additionally, the invented system 10 can be configured for use in multiple settings, which include, but are not limited to testing at remote (away from buildings) location, testing within a laboratory or test facility, and in-line testing in a manufacturing/production facility. Testing in a remote location is accommodated through use of a portable power supply, including, but not limited to, a vehicle's alternator, a portable generator, or a battery pack. This configuration could be utilized to support field testing and/or determination of material status prior to the usage of a device which the material is integrated to (e.g. a vehicle). Laboratory test setups can be integrated with a multi-axis linear motion scanning frame to enable the mapping of material properties and defect locations in one or more dimensions. This configuration could be utilized to perform failure analysis, quality control, or rapid development of novel materials. The disclosed invention may be integrated into a manufacturing setting to perform in-line quality assurance and/or quality control. This configuration could enable characterization of 100% of manufactured material to support production efficiency optimization to minimize material waste and manufacturing expenses.

Additional applications include, but are not limited to, material forensics, determination of RUL for condition-based maintenance, characterization of defects, microstructural mapping, acoustic/RF microscopy, structural health monitoring (SHM), and battle damage assessment (BDA).

The disclosed invention enhances material forensics applications where a user seeks to determine bulk properties and microstructural distribution nondestructively. The additional information provided by data fusion increases sensitivity to minute microstructural parameters and sub-resolution defects which can impact performance. The material information provided by application of the invention could facilitate product development by increasing the pace of developmental iterations.

Remaining useful life estimations are similarly improved by the higher resolution and finer detail provided by the invention. Finite element analysis models could be integrated with the microstructural parameter and material property outputs of the device to precisely determine whether a material will fail under given conditions and for what time period it could withstand a defined set of mechanical, thermal, and/or electrical stresses.

The defect signatures which are measured by the invention in both acoustic (elastic) and RF (electromagnetic) domains could be applied to enhance in-situ defect characterization. The invention could be utilized to identify specific defect geometry and composition which results from particular manufacturing processes to improve production efficiency and product quality.

Integration of the invention with a multi-axis scanning frame enables detailed bulk mapping of microstructural parameters which impact material properties and performance, such as grain size distribution, inclusion size distribution, property gradients, etc. The dimensionality of the maps equates with that of the scanning frame. Maps created with the invention could be utilized to determine material homogeneity and its relationship with manufacturing processes.

Integration of the invention within a system or structure enables SHM applications, whereby the invention could be used to monitor the integrity and properties of a material over time. The increased sensitivity to minute flaws provided by the invention enables the user to identify structural problems at an earlier stage than is possible with a single-technique approach. The early warning provided by such a system could prove invaluable in applications with a high likelihood of damages should a structure fail, such as avionics, civil engineering works, satellites, and other high value structures.

Application of the invention on material damaged by military or civil action could provide actionable information as to the status of the system which the material in integrated in, enabling condition-based maintenance of the system. Assessment of damage incurred could further be used to identify the cause of said damage, providing information which could be used to mitigate further damage in future altercations.

The above described multi-member approach combines acoustic and radio frequency (RF) NDE techniques to provide a complete assessment of the material properties while attaining superior sensitivity to minute structural defects.

Thus, the present invention has been described in such full, clear, concise and exact terms as to enable any person skilled in the art to which it pertains to make and use the same. It will be understood that variations, modifications, equivalents and substitutions for components of the specifically described embodiments of the invention may be made by those skilled in the art without departing from the spirit and scope of the invention as set forth in the appended claims.

We claim:

1. A system for determining properties and structural integrity of a material, said system comprising:
   (a) a first probe including:
      i. a first housing having a hollow interior,
      ii. a source of an acoustic energy mounted within said hollow interior and operable to emit a beam or a wave of said acoustic energy to enable it to interact with the material, and
      iii. a source of a radio frequency (RF) energy mounted within said hollow interior and operable to propagate said RF energy through the material thickness;
   (b) a second probe including:
      i. a second housing having a hollow interior
      ii. an acoustic member mounted within said hollow interior of said second housing, said acoustic member operable to capture said acoustic energy propagated through the material thickness and to generate an acoustic response signal, and
      iii. a radio frequency (RF) member mounted within said hollow interior of said second housing in a close proximity to said acoustic member, said RF member operable to capture said RF energy propagated through the material thickness and to generate an RF response signal;
   (c) a receiver coupled to said first and second probes and configured to receive said acoustic and RF response signals; and
   (d) a controller coupled to said receiver and including at least a processor operable to process said received acoustic and RF response signals and measure critical material properties while locating and identifying structural defects that degrade performance of the material.

2. The system of claim 1, further comprising a gantry and wherein each of said first and second probes is mounted for a linear reciprocal movement across a width of the material at least partially disposed within confines of said gantry.

3. The system of claim 2, wherein said gantry includes:
   (a) a frame;
   (b) a linear actuator mounted within said frame; and
   (c) wherein said each of said first and second probes is mechanically coupled to said linear actuator for said reciprocal linear movement across the width of the material.

4. The system of claim 3, further comprising a pair of spools configured to position the material in an operative alignment with said gantry.

5. The system of claim 1, wherein said processor is further operable to apply acoustic spectroscopy in at least one of identification of bulk material phases, determination of particle size distributions, and identification of characteristic defect signatures.

6. The system of claim 1, wherein said processor is further operable to process said received RF signals so as to verify and/or expand results determined from said received acoustic signals.

7. The system of claim 1, wherein said processor is further operable to analyze at least one of RF scattering parameter data, RF frequency domain data, RF time domain data, acoustic wave velocity data, acoustic wave time of flight data, acoustic received peak intensity data, and acoustic frequency dependent energy loss data.

8. The system of claim 1, wherein said processor is further operable to map location or locations of material properties in two or more dimensions.

9. The system of claim 1, wherein said processor is further operable to estimate a performance of the material based on the received acoustic and RF response signals.

10. The system of claim 1, wherein said acoustic member is operable in a range from about 20 kilohertz (kHz) to about 100 megahertz (MHz).

11. The system of claim 1, wherein said RF member is operable in a range from about 100 megahertz (MHz) to about 20 gigahertz (GHz).

12. The system of claim 1, wherein the material is one of a metal, a ceramic, a polymer, a composite, a multi-phase hybrid, a multi-layer hybrid and a combination thereof.

13. The system of claim 1, wherein said controller is operable to determine a correction factor due to inclusion of structural defects and use said correction factor in determining the properties of the material.

14. A method for determining properties and structural integrity of a material having multiple layers, said method comprising the steps of:

(a) emitting acoustic and radiofrequency (RF) energy into said material;
(b) receiving resulting acoustic and RF response signals;
(c) characterizing, with said acoustic and RF response signals, internal and/or surface defects of said material;
(d) determining, with said acoustic and RF response signals, a thickness of each individual layer;
(e) determining, with said acoustic and RF response signals, a correction factor for electromagnetic field propagation;
(f) defining, using said correction factor, electromagnetic field interactions; and
(g) extracting RF properties of said each individual layer.

15. The method of claim 14, wherein the step (c) includes the step of acquiring signatures of said defects.

16. The method of claim 14, wherein the step (c) includes the step of determining peak amplitudes of said acoustic response signal.

17. The method of claim 14, wherein the step (c) includes the step of conditioning said RF response signal.

* * * * *